(12) United States Patent
Fabo

(10) Patent No.: US 7,888,545 B2
(45) Date of Patent: Feb. 15, 2011

(54) SELF-ADHESIVE DRESSING

(75) Inventor: Tomas Fabo, Molnlycke (SE)

(73) Assignee: Mölnlycke Heath Care AB, Göteborg (SE)

( * ) Notice: Subject to any disclaimer, the term of this patent is extended or adjusted under 35 U.S.C. 154(b) by 759 days.

(21) Appl. No.: 11/794,476

(22) PCT Filed: Dec. 16, 2005

(86) PCT No.: PCT/SE2005/001949
§ 371 (c)(1),
(2), (4) Date: Sep. 18, 2007

(87) PCT Pub. No.: WO2006/071176
PCT Pub. Date: Jul. 6, 2006

(65) Prior Publication Data
US 2009/0270785 A1    Oct. 29, 2009

(30) Foreign Application Priority Data
Dec. 30, 2004   (SE) .................................... 0403213

(51) Int. Cl.
*A61F 13/00* (2006.01)
(52) U.S. Cl. .............................. 602/41; 602/45; 602/52
(58) Field of Classification Search ............... 602/41–54
See application file for complete search history.

(56) References Cited

U.S. PATENT DOCUMENTS

| 4,590,001 A | * | 5/1986 | Stjernholm | 530/394 |
| 5,635,201 A | * | 6/1997 | Fabo | 424/443 |
| 5,679,190 A | | 10/1997 | Riedel et al. | |
| 5,910,368 A | * | 6/1999 | Ehret | 428/411.1 |
| 6,500,539 B1 | * | 12/2002 | Chen et al. | 428/364 |

FOREIGN PATENT DOCUMENTS

WO    2005/112852    12/2005

* cited by examiner

*Primary Examiner*—Michael A. Brown
(74) *Attorney, Agent, or Firm*—Ballard Spahr LLP

(57) ABSTRACT

The present invention relates to a self-adhesive dressing comprising a layer (1) of spunlace nonwoven material and attached thereto a layer (2) of adhesive. In accordance with the invention, the dressing is stretchable in a first direction (MD) corresponding to the machine direction of the nonwoven material and in a second direction (CD) perpendicular to the first direction, in conjunction with which the resistance to stretching is less than 10 N/25 mm in both the first (MD) and the second (CD) directions in the case of stretching of less than or equal to 5%.

13 Claims, 2 Drawing Sheets

SELF-ADHESIVE DRESSING

TECHNICAL FIELD

The present invention relates to a self-adhesive dressing comprising a layer of spunlace nonwoven material and attached thereto a layer of adhesive.

BACKGROUND ART

Self-adhesive dressings of the above-mentioned type are commonly encountered and are used to secure compresses, tubes and other technical medical items to the skin. They can also include a compress integrated into the dressing and attached to the layer of adhesive.

Spunlace nonwoven material is manufactured by forming fibres into a mat by mechanical means, usually by carding, on a moving web, which then passes through a hydroentangling unit in which the web is subjected to a plurality of jets of water under high pressure. In the hydroentangling process, mixing of the fibres that have been laid on the web takes place together with attachment of the fibres to one another as a result of their being entangled with one another and becoming mechanically attached to one another (combined). Spunlace nonwoven material can also be produced from a moving web with a nap of air-laid or wet-laid fibres. Spunlace nonwoven material exhibits very good stretchability in a direction (CD) across the machine direction (MD), i.e. the direction of movement of the web of fibres through the hydroentangling unit, but significantly poorer stretchability in the machine direction (MD).

The major difference in the stretchability of spunlace nonwoven material in different directions constitutes a major disadvantage in conjunction with the use of such materials in self-adhesive dressings, especially if these are to be applied to or in the vicinity of joints, such as the knees, elbows, wrists or fingers and toes, in which the skin is subjected to considerable stretching. If such a material is applied incorrectly, i.e. if the machine direction (MD) of the nonwoven material coincides with the direction of stretching of the skin, the nonwoven material is not able to follow the movements of the skin at or close to a joint, and the dressing will move relative to the skin. A considerable risk is present of the skin being irritated or damaged in conjunction with such relative movement. Also, in the case of swellings and oedema, the dressing can cause damage to the skin if it is not able to follow the direction of stretching of the skin.

The purpose of the present invention is to solve this problem by making available a dressing of the above-mentioned type, which is also capable of following the movements of the skin at joints or in similar areas where the stretching of the skin can be considerable, including in the event that the machine direction (MD) of the nonwoven material in the applied dressing were to coincide with the direction of stretching of the skin.

DISCLOSURE OF INVENTION

The purpose of the invention is achieved by a self-adhesive dressing comprising a layer of spunlace nonwoven material and a layer of adhesive attached thereto, characterized in that the dressing is stretchable in a first direction (MD) corresponding to the machine direction of the nonwoven material and in a second direction (CD) perpendicular to the first direction, in conjunction with which the resistance to stretching is less than 10 N/25 mm in both the first (MD) and the second (CD) directions in the case of stretching of less than or equal to 5%.

In a first preferred embodiment, the quotient between the resistance to stretching in the first direction (MD) and the resistance to stretching in the second direction (CD) is equal to or less than 7 in the case of stretching of less than or equal to 5%. The nonwoven material is also pre-stretched in the second direction (CD) or pre-compressed in the first direction (MD), in conjunction with which the pre-stretching in the second direction (CD) is preferably 40-50% or the pre-compression in the first direction (MD) is 10-20%. The nonwoven material is constructed from staple fibres with a length exceeding 12 mm.

In a second preferred embodiment, a compress with a smaller area than the dressing is attached to the adhesive layer of the dressing.

BRIEF DESCRIPTION OF DRAWINGS

The invention is described below with reference to the accompanying Figures, in which.

MODE(S) FOR CARRYING OUT THE INVENTION

Figure 1:
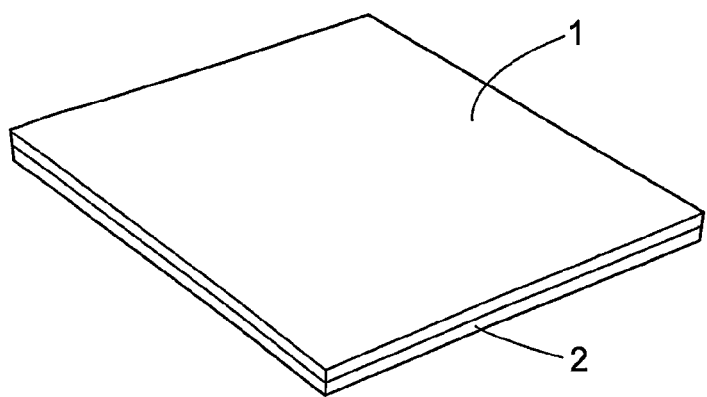
FIG. 1 illustrates schematically a preferred embodiment of a self-adhesive dressing in accordance with the invention.

Illustrated in FIG. 1 is an embodiment of a self-adhesive dressing in accordance with the invention. The dressing consists of a layer 1 of spunlace nonwoven and a layer 2 of adhesive. The nonwoven layer 1 is pre-stretched in the transverse direction (CD) or pre-compressed in the machine direction (MD) prior to the application of the adhesive layer 2. The adhesive layer of the dressing is covered in the customary fashion by a release layer, not illustrated here, for example a silicon-coated paper.

The pre-stretched or pre-compressed nonwoven layer consists of Sontara® 8010 (100% polyester) from Dupont, USA. Other spunlace materials constructed from other synthetic fibres can also be used. The constituent fibres must, if at all possible, have a length exceeding 12 mm.

Spunlace material is very stretchable in a direction (CD) perpendicular to the machine direction, that is to say the direction of movement of the web or the travelling wire on which the material is manufactured, but exhibits poor stretchability in the machine direction (MD). The poor stretchability in the machine direction is presumably attributable to the fact that the fibres during manufacture possess a tendency to align themselves in the machine direction. In order to improve the stretchability in the machine direction, the non-woven layer 1 is pre-stretched or pre-extended in the transverse direction (CD) or pre-compressed in the machine direction (MD), as previously mentioned, in accordance with the present invention. It has been established that such pre-stretching or pre-compression significantly increases the stretchability of the layer 1 in the machine direction in the finished dressing.

Pre-stretching means that the nonwoven material is stretched in the transverse direction and is kept stretched while the adhesive layer 2 is applied during manufacture of the dressing. Pre-compression will be described below with reference to FIG. 4, which illustrates a method for the manufacture of a self-adhesive dressing in accordance with the present invention.

Figure 2:
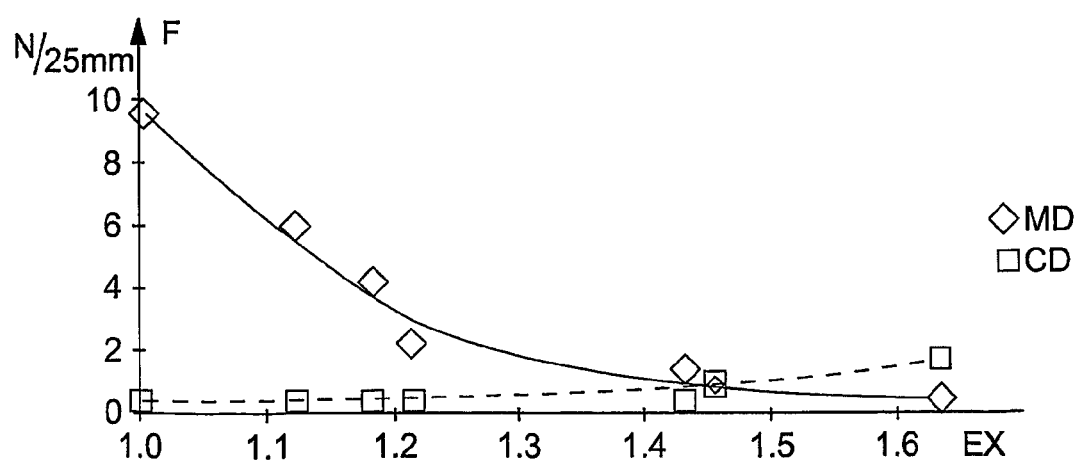
FIG. 2 shows a graph for the resistance to stretching for stretching a spunlace nonwoven material by 2% respectively in the machine direction (MD) and the transverse direction (CD) as a function of the stretching in the transverse direction (CD)

Shown in FIG. 2 is a curve representing the resistance to stretching as a function of the pre-stretching of the nonwoven material in the transverse direction. The resistance to stretching consisted of the force in N/25 mm required in order to cause a self-adhesive dressing in accordance with FIG. 1 to stretch by 2% in the machine direction. Measurement was performed by the following method. The resistance to stretching (N/25 mm) of a self-adhesive dressing consisting of unstretched Sontara® 8010 coated with an adhesive layer of acrylate adhesive under the trade name MG-0560/PA-560 from Cow Corning Corporation, Midland, Mich., USA, was measured first by cutting a first strip with a width of 25 mm in the transverse direction (CD) from the dressing and by then placing it between the jaws of a tensile testing machine, whereupon the force required to cause the first strip to stretch by 2% was measured. A similar was then performed with a second strip of the dressing with a width of 25 mm in the machine direction (MD). The measured forces F were 10 and 0.4 N/25 mm respectively. Similar measurements were then performed on dressings which differed from the dressing described above only in the sense that the nonwoven layer had been pre-stretched or pre-extended in the transverse direction (CD) to an increasingly higher degree before the adhesive layer was applied. The curves representing the force F/25 mm required in order to cause these dressings to stretch with different pre-stretching of the nonwoven layer by 2% in the machine direction and the transverse direction respectively are shown in FIG. 2. It can be appreciated from this Figure that the curves intersect one another for a pre-stretching of 48% in the nonwoven material, that is to say at a strip width equivalent to 1.48× the original width of the strip. The resistance to stretching, that is to say the force required to cause the strip to stretch by 2% with a 48% pre-stretched nonwoven layer, was thus equally high at this point of intersection in both the machine direction (MD) and the transverse direction (CD) and was measured as 0.8 N/25 mm.

Figure 3:
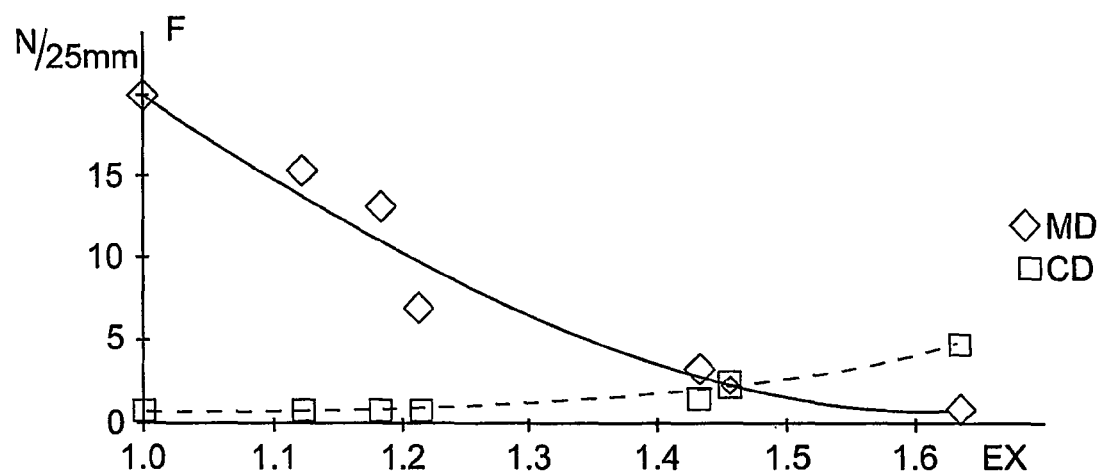
FIG. 3 shows a similar graph to that in FIG. 2 for 5% stretching.

Similar measurements were performed for the force required in order to cause similar strips to stretch, as described in conjunction with FIG. 2, by 5% instead of 2%, and the results are shown in FIG. 3. In this series of measurements, the force curves intersected one another with pre-stretching of the nonwoven material in the strips by 46% in the transverse direction, and the resistance to stretching at this point of intersection was 2.4 N/25 mm.

It can be appreciated from the measurements that it is quite easy to produce self-adhesive dressings with high stretchability in all directions. It can also be appreciated from the curves that the forces required in order to cause a dressing of this kind to stretch by 2% and 5% respectively in the machine direction and the transverse direction lie close to one another in the interval of 40-50% pre-stretching of the pre-stretched nonwoven layer contained in the dressing. By pre-stretching the spunlace nonwoven material in a dressing by 40-50% in accordance with the invention, it is thus possible to produce a self-adhesive dressing that is equally stretchable in all directions with a relatively small force for stretching of less than or equal to 5%.

In order to ensure that the force required to cause the dressing to stretch in different directions will not differ too much, the pre-stretching of the nonwoven material must be greater than 30%, and should preferably be 40-50%.

It is not necessary, however, for the force required to cause the dressing to stretch to be equally high in all directions, but it is sufficient for this force to be equal to or less than 10 N/25 mm in order for an applied dressing to be capable in a satisfactory fashion of accommodating any stretching of the skin that occurs. The difference between the forces for stretching respectively in the machine direction and in the transverse direction should not be too high, however. It is accordingly preferable for the quotient between the resistance to stretching in the machine direction and the resistance to stretching in the transverse direction to be equal to or less than 7 in the case of stretching of less than or equal to 5%, which is a considerable reduction compared with a dressing without a pre-stretched nonwoven layer, where this quotient is greater than 20, as can be appreciated from the curves in FIG. 3.

As can be appreciated from the illustrated curves, the resistance to stretching falls steeply in the machine direction in those dressings which contain pre-stretched nonwoven material. The pre-stretching should preferably be selected with a sufficiently high value to ensure that the resistance to stretching in the machine direction in a dressing containing pre-stretched nonwoven material, for stretching of 2-5%, reduces to less than ⅓ of the resistance to stretching in the case of a dressing which differs from such a dressing only in the sense that the nonwoven material contained in the dressing has not been pre-stretched.

The inner cohesion, adhesion force with the skin and adhesion force with the nonwoven material of the dressing adhesive must also be greater than the resistance to stretching of the nonwoven material in order for stretching of the nonwoven layer in the dressing to take place in the event of stretching of the skin. The above-mentioned adhesion forces relate to adhesion in the event of shearing loads and are significantly greater in the adhesives that are customarily used in such dressings than the forces required in order to cause the described dressings to stretch by up to 5%. The inner cohesion of such adhesives also meets the requirements indicated above.

The adhesive layer 2 in the self-adhesive dressing in accordance with FIG. 1 may consist of a PSA (Pressure Sensitive Adhesive) acrylate adhesive or of any adhesive of which the use is previously familiar in self-adhesive dressings or bandages, for example hydrogels or silicon gels.

The self-adhesive dressing in accordance with the invention can be manufactured by first attaching the edges of a nonwoven material facing in the machine direction to gripping devices, in conjunction with which these edges are then separated from one another by the agency of the gripping devices until the desired pre-stretching is obtained. While the nonwoven material is held securely by the gripping devices, the nonwoven material is then coated with adhesive and preferably also a release layer. Once individual dressings have been cut out, as required, the manufacture of the self-adhesive dressings in accordance with the invention is complete.

The resulting self-adhesive dressing or dressings can, if required, be sterilized at a later stage after having been packaged.

It has been found that stretching of a spunlace nonwoven material in the transverse direction is associated with a reduction in its length in the machine direction. The gripping devices must accordingly permit such shortening of the material.

Viewed in percentage terms, however, this shortening of the length in the machine direction is smaller than the extension of the length in the transverse direction, with the result that the nonwoven material after stretching in the transverse direction exhibits a greater area than before stretching, which means that the nonwoven material has become thinner as a consequence of stretching in the transverse direction. In the case of the above-mentioned Sontara® material, a 40% stretching of the material in the transverse direction is associated with a 15% reduction in its length in the machine direction.

The fact that spunlace nonwoven materials constructed from synthetic fibres only contain mechanical attachments produced by hydroentangling permits pre-stretching of the material in the transverse direction to take place without disturbing these mechanical attachments to any significant extent. The stretching performed in the transverse direction is achieved mainly by the bending in the transverse direction of fibres aligned in the machine direction, which takes place as a result of the stretching causing shortening of the material in the machine direction with an associated displacement of the bonds. Reorientation of fibres also takes place to a certain extent.

Figure 4:
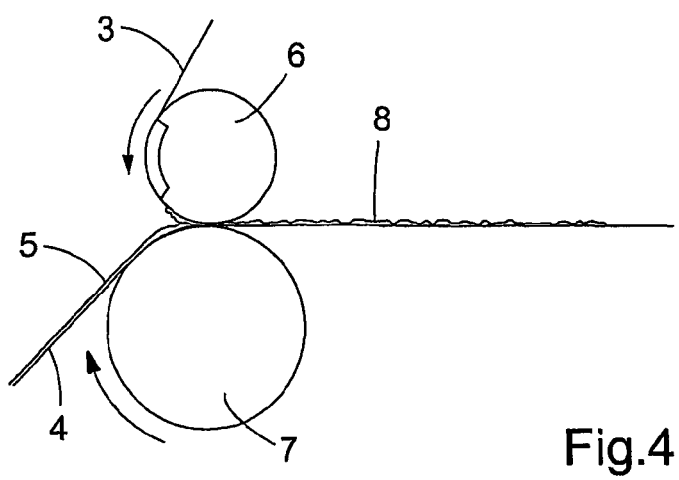
FIG. 4 illustrates schematically an arrangement for manufacturing a self-adhesive dressing, which is pre-compressed in the machine direction (MD).

Illustrated schematically in FIG. 4 is another means of increasing the stretchability in the machine direction in a spunlace nonwoven material. A web 3 of spunlace nonwoven material with a direction of movement coinciding with the machine direction of the material is fed in conjunction with a web 4, on which a layer 5 of adhesive is laid, through the nip between two rollers 6, 7 so that the web of nonwoven is attached to the adhesive layer. The roller 6, around the periphery of which the web 3 runs before entering into the nip between the rollers, rotates at a higher speed than the roller 7, so that its peripheral speed is greater than the peripheral speed of the roller 7. This means that the running speed of the nonwoven web 3 before entering into the nip between the rollers is higher than the running speed of the web 4 ahead of the nip between the rollers 6, 7. The webs 3 and 4 are attached to one another by means of the adhesive layer 5 in the nip between the rollers and move at the same speed, i.e. the running speed of the web 4, on exiting from the nip. The higher speed of the web 3 of nonwoven material than that of the web 4 imparts a greater length per unit of time for the nonwoven web than the length per unit of time for the web 4 with the applied adhesive layer 5. In order to compensate for this difference in length, nonwoven material accumulates in the area ahead of the nip between the rollers 6,7, and reorientation of the fibres in the nonwoven material takes place before entering into the nip between the rollers 6,7. Compression of the nonwoven material also takes place in conjunction with its passage through the nip between the rollers, so that any upward-projecting parts of fibres are bent or pressed down towards the web 4. After exiting from the nip between the rollers 6,7, the resulting web 8 consists of a nonwoven material compressed in the machine direction attached to an adhesive layer 5, which is in turn attached to a web 4. The web 4 can comprise a release material or a web coated with a substance that exhibits little adhesion to the layer 5, e.g. silicon. The web 8 can then be rolled up onto a roller or a plurality of rollers, or individual dressings can also be cut from the web. It is also possible to form weakening lines in the web, for example perforation lines, in order to permit the easy removal of individual dressings from a roll of dressings. If release material is to replace the web 4, this web is removed from the web 8 directly after its exit from the nip between the rollers 6,7, and the web 8 is provided with release material before the web of dressings is rolled up or individual dressings are cut out.

The difference in speed between the peripheral speeds of the rollers 6,7 is appropriately 10-20%, which provides a corresponding possibility for stretching in the machine direction for the manufactured dressings.

The pre-compression in the machine direction described above produces a self-adhesive dressing of adhesive-coated nonwoven material, which is also stretchable in the machine direction.

The described embodiments can naturally be modified within the scope of the invention. For example, the self-adhesive dressings can be provided with compresses having a smaller area than the nonwoven material and the adhesive layer. Other types of spunlace nonwoven can also be used, for example nonwoven material containing continuous filaments. The invention must accordingly only be restricted to the content of the following Patent Claims.

The invention claimed is:

1. A self-adhesive dressing comprising:
a layer (1) of spunlace nonwoven material and attached thereto a layer (2) of adhesive, wherein the dressing is stretchable in a first direction (MD) corresponding to a machine direction of the nonwoven material and in a second direction (CD) perpendicular to the first direction, in conjunction with which a resistance to stretching is less than 10 N/25 mm in both the first (MD) and the second (CD) directions in a case of stretching of less than or equal to 5%, and in that a quotient the resistance to stretching in the first direction (MD)

the resistance to stretching in the second direction (CD)

is equal to or less than 7 in the case of stretching of less than or equal to 5%.

2. The dressing in accordance with claim 1, wherein the nonwoven material is constructed from staple fibres with a length exceeding 12 mm.

3. The dressing in accordance with claim 2, wherein a compress with a smaller area than the dressing is attached to the adhesive layer of the dressing.

4. The dressing in accordance with claim 2, wherein the resistance to stretching in the machine direction of the dressing for a stretching of 2-5% is less than ⅓ of the resistance to stretching in the case of a dressing which differs from such a dressing only in the sense that the nonwoven material contained in the dressing has not been pre-stretched.

5. The dressing in accordance with claim 1, wherein a compress with a smaller area than the dressing is attached to the adhesive layer of the dressing.

6. The dressing in accordance with claim 5, wherein the resistance to stretching in the machine direction of the dressing for a stretching of 2-5% is less than ⅓ of the resistance to stretching in the case of a dressing which differs from such a dressing only in the sense that the nonwoven material contained in the dressing has not been pre-stretched.

7. The dressing in accordance with claim 1, wherein the resistance to stretching in the machine direction of the dressing for a stretching of 2-5% is less than ⅓ of the resistance to stretching in the case of a dressing which differs from such a dressing only in the sense that the nonwoven material contained in the dressing has not been pre-stretched.

8. A method for producing a self-adhesive dressing comprising a layer (1) of spunlace nonwoven material and attached thereto a layer (2) of adhesive, which dressing is stretchable in a first direction (MD) corresponding to the machine direction of the nonwoven material and in a second direction (CD) perpendicular to the first direction, characterized in that a layer of nonwoven material (1) is stretched in the second direction (CD) or is compressed in the first direction (MD), whereupon the nonwoven material (1) is coated with a layer (2) of adhesive.

9. The method in accordance with claim 8, wherein the layer (1) of nonwoven material is stretched by more than 30%, and preferably by 40-50%, in the second direction (CD).

10. The method in accordance with claim 9, wherein the stretching or the compression of the nonwoven material contained in the dressing is so great that the resistance to stretching in the machine direction of the dressing for a stretching of 2-5% is less than ⅓ of the resistance to stretching in the case of a dressing which differs from such a dressing only in the sense that the nonwoven material contained in the dressing has not been pre-stretched.

11. The method in accordance with claim 8, wherein the layer (1) of nonwoven material is compressed by 10-20% in the first direction (MD).

12. The method in accordance with claim 11, wherein the stretching or the compression of the nonwoven material contained in the dressing is so great that the resistance to stretching in the machine direction of the dressing for a stretching of 2-5% is less than ⅓ of the resistance to stretching in the case of a dressing which differs from such a dressing only in the sense that the nonwoven material contained in the dressing has not been pre-stretched.

13. The method in accordance with claim 8, wherein the stretching or the compression of the nonwoven material contained in the dressing is so great that the resistance to stretching in the machine direction of the dressing for a stretching of 2-5% is less than ⅓ of the resistance to stretching in the case of a dressing which differs from such a dressing only in the sense that the nonwoven material contained in the dressing has not been pre-stretched.

* * * * *